United States Patent
Lopata et al.

(10) Patent No.: US 6,607,894 B1
(45) Date of Patent: Aug. 19, 2003

(54) MATRIX METALLOPROTEINASE LEVELS AS INDICATORS OF ENDOMETRIAL CANCER

(76) Inventors: Alexander Lopata, 11 Clifton Street, Richmont, Victoria 3121 (AU); Lois A. Salamonsen, 11 McEvoy Street, Kew, Victoria 3101 (AU); Michael A. Quinn, 13 Wrixon Street, Kew, Victoria 3101 (AU)

(*) Notice: Subject to any disclaimer, the term of this patent is extended or adjusted under 35 U.S.C. 154(b) by 0 days.

(21) Appl. No.: 09/381,454
(22) PCT Filed: Mar. 20, 1998
(86) PCT No.: PCT/AU98/00189
§ 371 (c)(1), (2), (4) Date: Jan. 10, 2000
(87) PCT Pub. No.: WO98/42865
PCT Pub. Date: Oct. 1, 1998

(30) Foreign Application Priority Data

Mar. 20, 1997 (AU) .............................. PO 5736

(51) Int. Cl.[7] .................. G01N 33/48; G01N 33/53; G01N 33/573; G01N 33/574; C12N 9/50
(52) U.S. Cl. .................. 435/23; 435/7.1; 435/7.23; 435/7.4; 435/7.92; 435/188; 435/219; 435/226
(58) Field of Search ................. 435/7.23, 7.4, 435/23, 188, 219, 226, 7.1, 7.92; 424/94.1, 94.67, 558

(56) References Cited

U.S. PATENT DOCUMENTS 5,280,106 A * 1/1994 Liotta et al. ................ 530/330
5,482,848 A * 1/1996 Dickson et al. ............. 435/219

FOREIGN PATENT DOCUMENTS

WO    WO 93/20447    10/1993

OTHER PUBLICATIONS

Kikkawa, F. Regulation of matrix–degrading enzymes in gynecologic cancer tissues and cells, *Nippon Sanka Fujinka Gakkai Zasshi*, 48(8):618–622 (1996) (Abstract).

Soini, Y. et al. Expression of Messenger RNAs for metalloproteinases 2 and 9, type IV collagen, and Laminin in nonneoplastic and neoplastic endometrium, *Human Pathology* 28(2):220–226 (1997).

Tamakoshi, K. et al. Characterization of extracellular matrix–degrading proteinase and its inhibitor in gynecologic cancer tissues with clinically different metastatic form, *Cancer* 76(12):2565–2571 (1995).

Tamakoshi, K., et al. Different pattern of Zymography between human gynecologic normal and malignant tissues, *AM. J. Obstet. Gynecol.* 171(2):478–484 (1994).

* cited by examiner

*Primary Examiner*—Elizabeth Kemmerer
(74) *Attorney, Agent, or Firm*—Lahive & Cockfield LLP; Giulio A. DeConti, Jr., Esq.; Peter C. Lauro, Esq.

(57) ABSTRACT

This invention relates to methods for assaying the presence and/or risk of endometrial cancer by measurement of levels of matrix metalloproteinase-2 and/or matrix metalloproteinase-9 in uterine washings. The method may be qualitative or quantitative, and is adaptable to large-scale screening and to clinical trials.

40 Claims, 9 Drawing Sheets

| Lane | Sample Description | Sample Dilution |
|---|---|---|
| 1. | - | - |
| 2. | Molecular Weight Markers | 1:0 |
| 3. | L.S. (Endometrial Cancer) | Neat |
| 4. | " " | 1:2 |
| 5. | " " | 1:5 |
| 6. | " " | 1:10 |
| 7. | " " | 1:20 |
| 8. | " " | 1:50 |
| 9. | " " | 1:100 |
| 10. | - | - |

Fig. 1

ZYMOGRAPHY

| Lane | Sample Description | Sample Dilution |
|---|---|---|
| 1. | - | - |
| 2. | Molecular Weight Markers | 1:0 |
| 3. | B.F. (Endometrial Cancer) | 1:75 |
| 4. | A.K. (Endometrial Cancer) | 1:75 |
| 5. | L.S. (Endometrial Cancer) | 1:75 |
| 6. | - | - |
| 7. | B.F. (Endometrial Cancer) | 1:75 |
| 8. | A.K. (Endometrial Cancer) | 1:75 |
| 9. | L.S. (Endometrial Cancer) | 1:75 |
| 10. | - | - |

*Gel cut in half at lane 6
*Lanes 1-5 incubated with "normal" incubation buffer at 37°C
*Lanes 7-10 incubated with incubation buffer containing MMP inhibitors (5mM EDTA/2.5 mM Phenanthroline) at 37°C.

Fig. 2

ZYMOGRAPHY

| Lane | Sample Description | Sample Dilution |
|---|---|---|
| 1. | - | - |
| 2. | Molecular Weight Markers | 1:0 |
| 3. | V.Q. (Endometrial Cancer) | 1:40 |
| 4. | B.M. (Endometrial Cancer) | 1:40 |
| 5. | W.B. (Endometrial Cancer) | 1:40 |
| 6. | B.F. (Endometrial Cancer) | 1:40 |
| 7. | J.B. (Endometrial Cancer) | 1:40 |
| 8. | A.B. (Endometrial Cancer) | 1:40 |
| 9. | D.S. (Endometrial Cancer) | 1:40 |
| 10. | - | - |

Fig. 3A

| Lane | Sample Description | Sample Dilution |
|---|---|---|
| 1. | - | - |
| 2. | Molecular Weight Markers | 1:0 |
| 3. | F.S. (Control) | 1:10 |
| 4. | F.O. (Control) | 1:10 |
| 5. | D.R. (Control) | 1:10 |
| 6. | D.E. (Control) | 1:10 |
| 7. | S.S. (Control) | 1:10 |
| 8. | N.A. (Control) | 1:10 |
| 9. | J.F. (Control) | 1:10 |
| 10. | - | - |

Fig. 3B

ZYMOGRAPHY

| Lane | Sample Description | Sample Dilution |
|---|---|---|
| 1. | - | - |
| 2. | Molecular Weight Markers | 1:0 |
| 3. | V.Q. (Endometrial Cancer) | 1:40 |
| 4. | J.S. (Control) | 1:40 |
| 5. | C.N. (Control) | 1:40 |
| 6. | N.T. (Control) | 1:40 |
| 7. | C.N. (Control) | 1:10 |
| 8. | N.T. (Control) | 1:10 |
| 9. | - | - |
| 10. | - | - |

Fig. 4

ZYMOGRAPHY

| Lane | Sample Description | Sample Dilution |
|---|---|---|
| 1. | - | - |
| 2. | Molecular Weight Markers | 1:0 |
| 3. | B.M. (Endometrial Cancer) | 1:40 |
| 4. | M.R. (Endometrial Cancer) | 1:40 |
| 5. | A.K. (Endometrial Cancer) | 1:40 |
| 6. | B.F. (Endometrial Cancer) | 1:40 |
| 7. | S.S. (Control) | 1:40 |
| 8. | D.A. (Control) | 1:40 |
| 9. | V.S. (Control) | 1:40 |
| 10. | - | - |

Fig. 5

ZYMOGRAPHY

| Lane | Sample Description | Sample Dilution |
|---|---|---|
| 1. | Molecular Weight Markers | 1:0 |
| 2. | - | - |
| 3. | V.Q. (Endometrial Cancer) | 1:40 |
| 4. | C.M. (Endometrial Cancer) | 1:40 |
| 5. | P.T. (Endometrial Cancer) | 1:40 |
| 6. | J.F. (Control) | 1:40 |
| 7. | A.H. (Control) | 1:40 |
| 8. | J.I. (Control) | 1:40 |
| 9. | D.R. (Control) | 1:40 |
| 10. | F.S. (Control) | 1:40 |

Fig. 6

Optical Density

|   | 1 | 2 | 3 | 4 | 5 | 6 | 7 | 8 | 9 | 10 | 11 | 12 |
|---|---|---|---|---|---|---|---|---|---|----|----|----|
| A | 0.052 | 0.055 | 3.874 | 3.789 | 3.403 | 3.498 | 3.747 | 3.928 | 0.227 | 0.225 | 0.409 | 0.426 |
| B | 0.044 | 0.041 | 3.753 | 3.919 | 2.921 | 2.974 | 3.930 | 3.803 | 0.105 | 0.103 | 0.166 | 0.178 |
| C | 0.069 | 0.065 | 3.881 | 3.859 | 3.090 | 3.139 | 2.474 | 2.441 | 0.130 | 0.133 | 0.041 | 0.060 |
| D | 0.093 | 0.101 | 3.604 | 3.620 | 2.007 | 1.949 | 1.567 | 1.614 | 0.074 | 0.080 | 0.039 | 0.055 |
| E | 0.148 | 0.155 | 3.818 | 3.884 | 3.712 | 3.861 | 0.213 | 0.191 | 0.045 | 0.047 | 0.065 | 0.078 |
| F | 0.241 | 0.245 | 3.857 | 3.847 | 2.983 | 2.879 | 0.100 | 0.099 | 0.045 | 0.041 | 0.049 | 0.062 |
| G | 0.401 | 0.394 | 2.632 | 2.783 | 1.029 | 1.023 | 0.103 | 0.094 | 0.063 | 0.059 | 0.054 | 0.069 |
| H | 0.673 | 0.650 | 1.321 | 1.480 | 0.480 | 0.498 | 0.061 | 0.055 | 0.048 | 0.047 | 0.051 | 0.056 |

MATRIX METALLOPROTEINASE LEVELS AS INDICATORS OF ENDOMETRIAL CANCER

This application claims priority to international patent application Ser. No. PCT/AU98/000189, filed Mar. 20, 1998, and to Australian patent application PO 5736, filed Mar. 20, 1997.

This invention relates to methods for detection of cancer, and in particular to the detection of endometrial cancer. The method of the invention is amenable to large-scale screening, for example in women at increased risk of endometrial cancer.

BACKGROUND OF THE INVENTION

It is now clear that in many malignancies there is a high correlation between tumour aggressiveness and protease expression by the tumour cells. In the last seven years, for example, convincing evidence has accumulated that directly implicates members of the matrix metalloproteinase family in tumour invasion and metastasis.

Clinicians have long been aware of the need for developing objective criteria for the early detection of cancer, and for assessing prognostic factors when treating patients who have a malignant tumour. In general the stage of endometrial cancer, the degree of invasion into the myometrium, the histological grade and type of tumour, and the degree of invasion of the lymph-vascular space have some predictive value as to the aggressiveness of the disease. However, none of these factors is accurate, and all depend on subjective assessment. For example the type and grade of tumour are determined by histological examination, and it has been reported that assessment of these may result in a disagreement figure of up to 85% between individual different pathologists (Baak and Oort, 1991). Thus currently there is no means of predicting the prognosis for an individual patient.

It is becoming clear that the accurate prediction of the course of endometrial cancer, and the probability of survival following various types of treatment, also depend on the intrinsic properties of the malignant cells and their interaction with the host (Baak, 1991). A major objective of research in this field, therefore, is to discover the biological properties that determine the tumour's invasive and metastatic potential.

It is known from studies with other types of cancer that quantitative techniques related to tumour cell biology, such as DNA ploidy (Iversen, 1986; van der Putten et al, 1989; Berchuck et al, 1992; Podratz et al, 1993; Lukes et al, 1994), expression of E-cadherin which mediates cell-cell adhesion (Sakuragi et al, 1994), and the secretion of matrix metalloproteinases (MMPs) involved in cell invasion (Liotta et al, 1986; Stetler-Sevenson et al, 1993) can improve the assessment of prognosis and the prediction of survival, by providing reproducible objective measures related to the behaviour of the neoplastic cells. Alterations in cellular DNA content (ploidy) have been shown to correlate with biological behaviour in cancers of the ovary, breast, colon, lung and prostate (Seckinger et al, 1989), as well as in uterine malignancies (Moberger et al, 1985; van der Putten et al, 1989). In general, cancers with a normal diploid DNA content have a better prognosis than cancers with an abnormal, aneuploid or polyploid DNA content. Determination of DNA ploidy in endometrial and other cancers has therefore become a powerful tool for assessing prognosis and the probability of survival in relation to recurrence of the disease, and is a better predictor than molecular or genetic markers (Lukes et al, 1994).

It is now clear that in many malignancies there is a high correlation between tumour aggressiveness and expression of proteases in the tumour tissue. In the last seven years, for example, convincing evidence has accumulated that directly implicates members of the matrix metalloproteinase (MMP) family and tissue inhibitors of metalloproteinases (TIMPs) in tumour invasion and metastasis (reviewed by Stetler-Stevenson et al, 1993). It has been suggested that detection of MMPs in biological fluids, especially as complexes with TZMPs, can be used to detect metastatic cancer (U.S. Pat. No 5,324,634 by Zucker). These enzymes are also synthesised and secreted by normal cells during physiological tissue remodelling (menstruation) and invasion (embryo implantation) (Salamonsen, 1995, 1996). MMPs may be present in tissues either in the fully active form, or in a latent form which requires activation before enzymic activity can be demonstrated.

We have recently established that MMPs are released into the uterine cavity during the ovarian cycle and early pregnancy in marmoset monkeys (our unpublished results). Moreover, over-expression of these enzymes has been reported to occur in many tumour cells, for example those of colorectal and squamous cell carcinomas.

Recently it has been demonstrated that ovarian cancer cells, but not normal ovarian epithelial cells, secrete enhanced levels of matrix metalloproteinases similar to MMP-2 and MMP-9, which directly degrade basement membrane proteins (Moser et al, 1994; Salamonsen, 1996). This proteolytic capability was correlated with the invasive potential of the ovarian malignancies. Furthermore, immunohistochemistry employing monoclonal antibodies has been used to localize MMP-2 to the cytoplasm and plasma membranes of various neoplastic cells, including endometrial cancers, whereas TIMP-2 was localized mainly to the stroma of these tissues (Hoyhtya et al, 1994). Apart from this, little is known about the expression of HMPs and TIMPs in endometrial cancers. Such information is essential for developing strategies for controlling the biological behaviour of endometrial and other types of malignancies.

We have now unexpectedly discovered that matrix metalloproteinases can be detected in uterine washings from patients with endometrial cancer, but not in similar washings from control women. This finding makes possible a sensitive diagnostic test which can be performed with minimal invasion, and a screening test which may be utilised for screening at-risk populations or the general population, or for use in clinical trials of putative treatments. The test is also suitable for monitoring the efficacy of treatment and for detection of recurrences.

SUMMARY OF THE INVENTION

In one aspect, the invention provides a method of assaying for the presence and/or risk of endometrial cancer, comprising the steps of obtaining a sample of uterine washings from a subject at risk of, or suspected to be suffering from, endometrial cancer, and measuring the levels of matrix metalloproteinases (MMPs) in the washings.

For the purposes of this specification, the expression "detection of endometrial cancer" is used in its broadest sense, and includes the determination of the likely presence or absence of cancer, or cells in a precancerous state or the early phases of development of cancer. Thus the invention encompasses not only the detection of active endometrial cancer, but also the risk of developing such active cancer.

The uterine washings may be obtained by using any suitable solution which is delivered to the uterine cavity and then recovered and collected for testing. Suitable solutions will be readily apparent to those skilled in the art and include any sterile non-toxic solution which will not interfere with measurement of MMPs. An example of a suitable solution is sterile saline. Any number of means for delivery and recovery of the washing solution may be utilised, by way of example a syringe and tube are conveniently used. The washing may be collected in the recovery means or transferred to another container. Delivery, recovery and collection means will routinely be chosen to provide comfort and convenience to both the patient and clinician.

Any suitable technique for determining levels of MMPs in the washings may be employed in the method of the invention. Examples of suitable techniques include those based on determining enzyme activity, and/or those based on determining the presence or levels of enzyme. Total MMPs, including latent, active, and TIMP-bound MMP, may be measured. Those skilled in the art will readily be able to determine whether or not a technique is suitable, if necessary using positive and negative control samples. For example, gelatin zymography is suitable for detection of all forms of MMP-2 and MMP-9. Optionally the zymographic assay may be coupled with densitometry in order to provide a semi-quantitative assessment of each enzyme type and form (ie. latent or active). Active enzyme may also be assayed using substrate-based activity assays.

Total gelatinolytic activity present in the uterine washings may be measured; although this does not distinguish between the different types of MMPs present, it does produce a quick estimate of total MMP activity. However, preferably the level of activity of MMP-2 and/or MMP-9 is measured.

Alternatively total enzyme levels may be measured using methods such as ELISA, fluorometric assay, chemiluminescent assay, or radioimmunoassay. BLISA or chemiluminescent assay methods are particularly preferred, since these are quick, sensitive, and specific, and are readily automated for large scale use. These methods also provide quantitative determinations. A number of appropriate methods for measuring these enzymes are detailed in Barrett (1995).

Optionally levels of tissue inhibitors of metalloproteinases (TINPs) may also be determined in the uterine washings, for example by reverse zymography or ELISA.

In an additional embodiment of the invention, a sample of superficial endometrial cells is collected at the same time as the uterine washings are obtained, for example by insertion of a uterine brush into the uterine cavity, the endometrial cells are subjected to cytological examination for determination of ploidy and nuclear morphometry, and levels of MMPs, determined as described above, are correlated with DNA ploidy as an indicator of the prognosis of endometrial cancer when endometrial cancer is present.

Standard image cytometry techniques and automated equipment may be used for determination of ploidy and nuclear morphology.

In a second aspect, the invention provides a method for assessing the prognosis of endometrial cancer, comprising the steps of measuring MMP activity in uterine washings obtained prior to surgery in a patient undergoing surgery for endometrial cancer, obtaining a sample of endometrial cells from said patient, obtaining a sample of tumour and adjacent normal endometrium for histological examination, and correlating MAP activity, DNA ploidy and grade and type of tumour as an indicator of the prognosis.

If surgery to remove the uterus is not possible for any reason, primary treatment of endometrial cancer may be conservative, using radiotherapy, chemotherapy, endometrial ablation (for example, using photo dynamic therapy, or curettage, rather than hysterectomy); in some cases curettage is used in conjunction with other methods. In patients undergoing such conservative treatment, follow-up and detection of recurrence of cancer is particularly important.

Thus in a third aspect, the invention provides a method of monitoring the efficacy of treatment of endometrial cancer, comprising the steps of obtaining a sample of uterine washings from a patient undergoing such treatment, and measuring the levels of MMPs in the washings. This method is also applicable to monitoring efficacy of putative treatments.

In a fourth aspect, the invention provides a method of detecting recurrence of endometrial cancer in a patient who has undergone conservative treatment for primary endometrial cancer, comprising the steps of obtaining a sample of uterine washings from the patient, and measuring the levels of MKPs in the washings.

Preferably the activities of MMP-2 and MMP-9 are determined by quantitative densitometric zymography or ELISA, as described above.

The method of the invention is suitable for screening of asymptomatic or well women, or of at-risk populations, such as diabetic women or women undergoing post-menopausal hormone replacement therapy.

In a fifth aspect, the invention provides a kit for assaying the presence and/or risk of endometrial cancer, comprising:

(a) a suitable solution for washing the uterine cavity, and (b) a means for delivery, recovery and collection of the uterine washings.

Preferably the kit further comprises:

(c) a means for determining the level of MMPs in said washings.

The kit may further optionally include one or more of:

(d) a means for taking a sample of endometrial epithelium, (e) one or more microscope slides, and (f) a receptacle containing a histological fixative.

In one preferred embodiment, the kit comprises:

(a) a sterile physiologically-acceptable solution for washing the uterine cavity, (b) a sterile syringe, (c) a sterile feeding tube or catheter, (d) a receptacle for uterine washings, and optionally, (e) a uterine brush, and/or (f) one or more microscope slides.

Preferably the kit additionally comprises a receptacle containing a histological fixative; more preferably the fixative is 4% paraformaldehyde.

For the purposes of this specification it will be learly understood that the word "comprising" means "including but not limited to", and that the word "comprises" has a corresponding meaning.

BRIEF DESCRIPTION OF THE FIGURES

FIG. 3 compares zymographic results obtained using samples of uterine washings in patients with endometrial cancer (FIG. 3a) with samples from control subjects (FIG. 3b). The control samples were loaded at a concentration four times those of the samples from the cancer patients.

DETAILED DESCRIPTION OF THE INVENTION

Patients

The invention will now be described in detail by way of reference only to the following non-limiting examples, and to the Figures.

Nearly all patients who have surgical treatment for endometrial cancer at the Royal Women's Hospital are included in the study group (Table 1).

Women who have surgical or diagnostic procedures for other conditions, and have given consent to a uterine irrigation, are included in the control group To increase the size of the study populations more quickly, patients being treated for uterine cancer at the Mercy Hospital are also included.

One study population comprises postmenopausal and perimenopausal women who are being investigated for uterine bleeding. In these patients a vacuum irrigation of the uterine cavity is performed before the diagnostic hysteroscopy and dilatation and curettage are performed.

The second population comprises women who are having surgery for endometrial cancer. In this group the uterine cavity is irrigated at the start of surgery.

A third population comprises asymptomatic women, in the same age range as the previous study groups, who would have a uterine irrigation and endometrial epithelial cytology as a control group.

In all cancer patients the following samples are being collected for the studies described herein:

(1) A cell-free supernatant of uterine washings for analysis of secreted enzymes (MMPs) and their inhibitors (TIMPs) by zymography. To date MMP-2 and MMP-9 have been examined by gelatin zymography (Table 1), ELISA and immunoblotting. Our determinations of MMP-1 and MMP-3 using casein zymography have shown that these enzymes are absent, or are released at very low levels into uterine secretions.

(2) Endometrial cells for determination of DNA ploidy: In each patient such cells are obtained from the cell pellet derived from uterine washings, from endometrial epithelium recovered with a uterine brush, and from touch imprints of the malignant tumour or microscope slides. Each preparation has been used for ploidy analysis, and consistent results have been obtained from the three methods employed. Ploidy determinations have been previously reported to provide an objective and reproducible parameter for assessing prognosis in cancer patients.

(3) Pieces of tumour and adjacent normal endometrium are fixed in Carnoy's fixative and in paraformaldehyde. Histological sections of these tissues are studied for the presence of MMPs by immunohistochemistry, and for the transcription of genes for these enzymes and inhibitors using in situ hybridisation. Samples of tumour and adjacent normal tissue from some patients are also frozen for subsequent further study, eg. direct analysis of MKPs in tissue.

Collection of Uterine Fluid and Cells

A syringe containing 5 ml of saline is attached to a feeding tube. The feeding tube is inserted through the cervix and the uterine cavity is irrigated, and the fluid collected back into the syringe is transferred to a test tube. A uterine brush is also inserted into the uterine cavity, and superficial endometrial cells are collected for cytology.

The uterine fluid is centrifuged at 3000 rpm for 10 minutes. Aliquots of the supernatant are collected and stored at $-80°$ C. for subsequent MMP/TZMP analysis. The pellet of endometrial cells and the endometrial cytology sample obtained from the uterine brush are smeared on to slides coated with 2% 3-aminopropyltriethoxy silane (AAS). These cytological slides are fixed in 4% paraformaldehyde and then Feulgen stained for the assessment of DNA ploidy using image cytometry.

Processing of Uterine Contents

In the cancer and control study groups the uterine washings are immediately centrifuged at 3000 rpm for 10 mins to pellet the cells and the supernatant is frozen for subsequent MMP and TIMP studies. The cell pellet from both groups is prepared for determination of DNA ploidy using image cytometry as described below. In patients undergoing surgical resection for endometrial cancer the following samples are prepared. After the resected uterus is opened at least two touch preparation are taken from the surface of the tumour for DNA ploidy determinations, as with the cell pellet. In addition, a sample of malignant tissue, particularly in an area of invasion, and a sample of adjoining normal endometrial tissue are excised for immunohistochemical and in situ hybridisation studies before the remainder of the uterus is processed for histopathological examination. The latter includes assessment of depth of myometrial invasion, as well as grade and type of tumour. In addition the presence or absence of lymph node and adnexal metastasis are determined.

DNA Ploidy Studies

The pellet of desquamated epithelial cells obtained from the uterine washings is dispersed, washed with culture medium, resuspended and filtered through a 60 $\mu$m nylon mesh filter. The suspension of cells is affixed to polylysine-coated glass slides by cytospin centrifugation. In these preparations and for the touch imprints of uterine tumours a computerised optical image analysis system is used to quantitate Feulgen staining of DNA. The instrument is calibrated using cells that have a known amount of DNA (rat hepatocytes), which have been stained along with the test samples at one end of the slide. Between 200 and 300 cells are selected and analysed. As individual nuclei are scanned histograms of the DNA content per cell are generated, and determination of ploidy is made on the basis of these histograms by the location of the main and secondary peaks (diploid DNA index 1.0±0.1).

Analysis of MMPs and TIMPs in Uterine Washings

Enzyme activities in uterine washings are analyzed by gelatin (WP-2, MMP-9) or casein (MMP-1, MMP-3, MMP-7) zymography. Samples are subjected to SDS-PAGE on 10% acrylamide gels containing either gelatin or casein (each 1 mg/ml) under non-reducing conditions. After washing in buffer containing 50 mmol/L Tris-HCl, 5 mmol/L $CaCl_2$, $NaN_3$, 0.02% (w/v; pH 7.5) and 1% Triton X-100, the gels are incubated in the same buffer without Triton at 37° C. for 2–24 h, and stained with Coomassie Brilliant Blue. Gelatinase or caseinase activity is visualised by negative staining of the gel. Both latent and active MMPs are detected by this technique, because the SDS activates the latent MMPs. Where appropriate, MMP inhibitors are added during incubation (5 mmol/L EDTA and 2.5 mmol/L o-phenanthroline). For quantitation, in order to compensate for the wide variability in the protein content of the uterine washings between individuals, the volume loaded is related to the total volume of the uterine washing fluid, thus enabling assessment of relative MMP concentrations in the uterine lumen of each individual. The gels are subjected to densitometric analysis using a HP Desk Scanner with Deskscan software and the NIH Image program version 1.54 fitted with gel plotting macros, by measuring the area beneath the peaks plotted through the lane profile for either the enzyme of interest or for an individual sample. Quantitative comparisons are made only within a gel or a set of gels, poured and run in parallel. Each gel contains at least two dilutions of a standard, and each set of gels contains four dilutions of this standard. Where activities of an enzyme of interest are very high, samples are further diluted and rerun. The use of zymography in this way as a quantitative technique has been described (Kleiner & Stetler-Stevenson, 1994, and references listed therein). The technique is very sensitive, the detection limit being much lower than with methods such as ELISA which have a detection limit in the ng per sample range, and for both MMP-2 and MMP-9 the detection limit is of the order of 2 pg per sample (1 nM).

Gelatinase Activity Assay

This assay involves incubation of the sample with a $^{14}C$-labelled collagen substrate. The substrate is isolated from guinea pig skin, dialysed, labelled with $^{14}C$ and just before use, is heat denatured at 60° C. for 20 mins to be converted to a form, $^{14}C$-gelatin, that can be digested by the enzymes MMP-2 and MMP-9.

Total gelatinolytic activity is measured by incubating the substrate with 100 μg/ml of trypsin. The samples are either untreated, or preincubated with aminophenyl mercuric acetate to activate latent MMPs. The assay samples are incubated at 37° C. for 4–24 hrs, and the reaction is quenched by the addition of 30% trichloroacetic acid/1% tannic acid. A precipitate of any undigested substrate is formed. Any enzyme activity is measured by counting the amount of labelled substrate digested and released into the supernatant. Using this assay system, it is possible to calculate specific activity in each sample; one unit of activity is defined as the amount of enzyme capable of degrading 1 μg substrate per minute at 37° C. The assay is useful in defining both the enzyme activity already active in the sample, and the activity potentially available following activation of latent enzyme; in physiological terms this would represent the rate at which the enzyme in the sample is degrading the extracellular matrix components. The assay only measures total gelatinase activity; it does not distinguish between the activity of gelatinases such as MMP-2 and MMP-9. The specific MMPs may be differentiated by zymography.

Immunohistochemistry and in Situ Hybridisation

Specific reagents and methods for analysis of MMPs and TIMPs have been described in the literature (for example, Rawdanowicz et al, 1994; Jeziorska et al, 1996; Salamonsen and Woolley, 1996). Antisera are now available commercially (for example from Biogenesis Ltd, U.K., Triple Point Biologics, Oreg. U.S.A., The Binding Site, U.K.) and pure enzymes and TIMPs are also available (Calbiochem, Cambridge Mass., U.S.A.). All the relevant genes have been cloned, and the sequences are published and available in the public domain.

Immunohistochemistry is performed on Carnoy's-fixed or paraformaldehyde, wax-embedded tissues using the antisera detailed above and the alkaline phosphatase/anti-alkaline phosphatase (APAAP) detection system (Serotec) (Salamonsen et al, 1991; Salamonsen et al, 1993; Rawdanowicz et al, 1994). Paraformaldehyde fixation is generally more convenient, and gives better results for small samples. In situ hybridisation uses digoxygenin-labelled DNA or RNA probes.

EXAMPLE 1

MMPs Released into the Uterine Cavity in Patients Being Investigated for Endometrial Cancer Samples from 52 patients with endometrial cancer and 40 control patients undergoing diagnostic procedures for uterine bleeding or for other gynaecological conditions were examined for MMP-2 and MMP-9 by zymography and for DNA ploidy of superficial endometrial cells by image cytometry. For the patients found to have endometrial cancer the grade of malignancy was assessed. MMP-2 and MMP-9 were resolved further, into the following putative molecular types: latent MMP-2, active MMP-2, dimeric MMP-9, glycosylated pro MMP-9 and active MMP-9. The identities of latent and active MMP-2 and MMP-9 were subsequently confirmed, as described in a later example.

The results are summarised in Tables 1 and 2. In addition, MMP-1, MMP-3 and MMP-7 were measured using casein zymography, but detectable levels were not found in either the control or the endometrial cancer uterine washings.

Table 1 summarises zymography results obtained in patients with endometrial cancer of various grades in relation to other clinical and pathological parameters in this group. The gelatinase zymography resolved two molecular forms of MMP-2 and three molecular forms of MMP-9. To date the weakest gelatinolytic activity detected in the uterine washings from endometrial cancer revealed one form of MMP-2 (assigned+) and two forms of MMP-9 (both assigned +), in the patient coded J.O. If a total of three pluses, scored as the sum of any of the MMP moiety levels, is set as the minimum level required for a positive diagnosis of endometrial cancer, none of the controls shown in Table 2 would be diagnosed as a false positive. To date no false negative results (absence of any MMP activity) have been encountered in the endometrial cancer group. In terms of individual uterine washings from cancer patients the level of gelatinolytic activity observed ranged from 3 to 22 pluses.

TABLE 1

Summary of current results comparing various parameters in patients with endometrial cancer.

| Patient Name | Age | Grade | DNA Ploidy Status | Malignancy Grade# | Nodal Involvement | Vascular Invasion | Depth of Myometrial Invasion | latent MMP-2 | active MMP-2 | putative dimeric MMP-9 | pro-MMP-9 | active MMP-9 |
|---|---|---|---|---|---|---|---|---|---|---|---|---|
| | | | | | | | | \multicolumn{5}{c}{MMP Expression*} |
| B. F. | 58 | 1 | polyploid | 0.93 | no | no | >1/3 (mostly 2 mm) | ++ | ++ | +++ | ++++ | ++++ |
| M. R. | 50 | 1 | diploid | 0.34 | no | yes | Superficial (5/27) | +++ | + | ++++ | ++++ | ++++ |
| S. H. | 57 | 1 | diploid | 0.03 | no | yes | <1/3 | + | − | + | +++ | + |
| B. M. | 59 | 1 | diploid | 0.26 | no | no | Superficial (1/10) | ++ | + | ++++ | +++++ | +++ |
| W. B. | 72 | 1 | polyploid | 1.39 | no | no | 2.8 mm from serosa | +++++ | +++ | ++++ | +++++ | +++ |
| V. Q. | 58 | 1 | diploid | 0.17 | no | yes | Superficial | ++++ | +++ | +++ | ++++ | + |
| A. K. | 58 | 1 | diploid | 0.48 | no | yes | 7/8 | +++ | ++ | + | ++++ | + |
| C. H | 54 | 1 | diploid | 0.16 | no | no | 4/13 (inner third) | ++ | + | ++++ | ++++ | +++ |
| J. E | 62 | 1 | diploid | 0.29 | no | no | 5/15 | + | + | ++ | +++ | + |
| A. K. | 65 | 1 | diploid | 0.13 | no | no | inner half | +++ | + | +++ | +++++ | ++++ |
| C. M. | 67 | 1 | diploid | 0.34 | no | yes | 2/3 | +++++ | +++ | +++++ | +++++ | +++ |
| J. Q. | 57 | 1 | diploid | 0.21 | yes | yes | 8/22 | ++++ | − | ++ | ++++ | + |
| N. K. | 73 | 1 | diploid | 0.05 | no | no | 1/32 | ++ | − | + | ++ | − |
| Z. K. | 53 | 1 | diploid | 0.07 | no | no | 1/11 | ++ | + | + | + | + |
| S. S. | 49 | 1 | diploid | 0.09 | yes | no | 5/32 | +++ | + | + | ++ | − |
| D. R. | 67 | 1 | polyploid | 0.53 | no | no | Superficial (2/3) | + | ++ | +++ | ++ | ++ |
| M. T. | 73 | 1 | polyploid | 3.00 | no | no | Superficial | + | + | − | ++ | − |
| G. M.. | 67 | 1 | diploid | 0.16 | no | no | 1 mm Into adjacent myometrium | + | +++ | + | ++ | − |
| T. O'T. | 84 | 1 | polyploid | 0.48 | no | yes | 12/15 | +++ | − | + | ++++ | + |
| R. F. | 64 | 1 | diploid | 0.02 | — | no | 7/26 | ++ | + | +++++ | +++++ | +++ |
| L. H. | 62 | 1 | — | — | — | no | 0 | +++++ | +++ | ++++ | +++++ | +++++ |
| C. T. | 73 | 1 | diploid | 0.08 | — | no | 4/18 | − | − | + | ++ | + |
| L. C. | 53 | 2 | polyploid | 1.72 | no | no | <inner third | +++ | − | ++ | ++++ | + |
| J. O. | 55 | 2 | polyploid | 0.54 | no | no | 0 | + | − | + | + | − |
| V. D. | 60 | 2 | diploid | 0.16 | no | no | 5/13 | ++ | − | ++ | +++ | ++ |
| D. S. | 55 | 2 | diploid | 0.13 | no | yes | Superficial | ++ | − | +++ | +++ | + |
| P. T. | 65 | 2 | polyploid | 0.58 | yes | yes | 2.8 mm from serosa | +++ | + | ++++ | +++++ | + |
| A. B. | 60 | 2 | diploid | 0.17 | no | yes | full thickness | ++ | + | ++ | +++ | + |
| J. B. | 72 | 2 | polyploid | 1.55 | yes | no | >2/3 | ++++ | ++ | +++ | +++++ | ++ |
| B. R. | 55 | 2 | diploid | 0.05 | no | no | <1/3 | +++ | ++ | ++ | +++++ | ++++ |
| D. W. | 63 | — | polyploid | 1.57 | no | no | 2/13 | +++ | ++ | ++ | +++ | + |
| I. F. | 68 | 2 | polyploid | 0.77 | no | no | 11/27 | ++ | +++ | − | ++ | − |
| D. M. | 54 | 2 | polyploid | 2.31 | — | yes | 8/24 | ++ | +++ | + | +++ | + |
| E. H. | 75 | 2 | — | — | yes | no | within 5 mm of serosa | +++ | ++ | +++++ | +++++ | +++ |
| C. C. | 51 | 2 | diploid | 0.72 | no | no | 9/19 | ++ | ++ | − | + | − |
| M. S. | 73 | 2 | polyploid | >3 | no | no | 5/13 | + | ++++ | + | ++++ | − |
| D. S. | 63 | 2 | — | — | no | no | 1/21 | +++ | − | + | +++ | + |
| D. K. | 57 | 2 | polyploid | >3 | yes | yes | >inner 2/3 | ++ | + | ++++ | +++++ | +++ |
| E. L. | 61 | 2 | diploid | 0.03 | yes | yes | 12/21 | ++ | − | +++++ | +++++ | +++ |
| L. R. | 62 | | | "Grade 2 on curetting" | | | | ++ | − | +++ | ++++ | + |
| C. G. | 63 | 2 | diploid | 0.28 | yes | yes | 17/16 | ++++ | +++ | ++++ | +++++ | +++ |
| C. S. | 60 | 2 | polyploid | 2.07 | — | yes | Superficial (2/11) | ++ | − | ++ | ++ | ++++ |
| K. K. | 64 | | | "Grade 3 on curetting" | | | | − | ++ | − | + | − |
| C. S. | 68 | 3 | diploid | 0.03 | no | no | >inner 1/3 (minimal) | − | ++ | − | + | − |
| R. B. | 76 | 3 | polyploid | 2.44 | no | no | 2/12 | + | +++ | − | ++ | − |
| L. D | 63 | 3 | diploid | 0.36 | no | yes | 10/17 | ++ | − | − | +++ | + |
| T. B. | 94 | | "uterine curetting shows squamous cell carcinoma in situ and occasional fragments showing invasive squamous cell carcinoma. No TAH was performed due to age of the patient and overall health" | | | | | ++ | ++ | + | ++ | − |
| O. L. | 79 | — | polyploid | 0.4 | | Polyploid rhabdomyosarcoma | | ++ | − | − | +++ | + |
| A. J. | 58 | 3 | polyploid | >3 | no | no | Superficial (4/17) | +++ | + | +++ | +++++ | + |
| L. S. | 79 | 3 | diploid | 0.53 | no | no | inner half | +++ | + | +++++ | +++++ | ++++ |

TABLE 1-continued

Summary of current results comparing various parameters in patients with endometrial cancer.

| Patient Name | Age | Grade | DNA Ploidy Status | Malignancy Grade[#] | Nodal Involvement | Vascular Invasion | Depth of Myometrial Invasion | MMP Expression* | | | | |
|---|---|---|---|---|---|---|---|---|---|---|---|---|
| | | | | | | | | latent MMP-2 | active MMP-2 | putative dimeric MMP-9 | pro-MMP-9 | active MMP-9 |
| I. F. | 54 | 3 | diploid | 0.25 | no | yes | inner half | + | − | + | ++ | + |
| H. M. | 68 | 3 | diploid | 0.35 | — | yes | 0/15 | +++++ | + | − | +++ | − |

*All uterine irrigation samples were diluted 1:40;
Zymography results based on a scoring system related to size and density of enzyme bands: none (−), very low (+), low (++), moderate (+++). high (++++), very high(+++++).
[#]Malignancy is represented on a scale that ranges from 0.01 to 3.0. Tumours associated with a low malignancy grade (between 0.01 and 1.0) have been correlated with a high survival rate, tumours with a malignancy grade between 1.1 and 1.9 have a moderate survival rate, while tumours with a high malignancy grade (between 2.0 and 3.0) have shorter mean survival times. Bocking A, et al., Algorithm for a DNA-cytophotometric diagnosis and grading of malignancy. Anal. Quant. Cytol. 6(1): 1–8, 1984.

Table 2 summarises zymography results obtained in the control patients (no clinically detectable endometrial cancer), as well as other clinical and pathological parameters in this group. The gelatinase zymography revealed the presence of a very low level of latent MMP-2 in five patients and a very low level of the 120 kDa gelatinase (putative MMP-9) in one patient. To date no other forms of MMP were detected in uterine washings diluted for the zymography assays. The absence of detectable gelatinolytic activity in the uterine washings of the majority of control patients, or very low activity of a single molecular form of MMP, scored as a maximum of one plus, suggests that when several MMP moieties are detected in the uterine washings a specific and sensitive diagnosis of endometrial cancer may be made.

TABLE 2

Summary of current results comparing various parameters in the control group.

| Patient Name | Age | DNA Ploidy Status | Clinical Notes | MMP Expression* | | | | |
|---|---|---|---|---|---|---|---|---|
| | | | | latent MMP-2 | active MMP-2 | putative dimeric MMP-9 | pro-MMP-9 | active MMP-9 |
| F. O. | 46 | — | uterine adenomyosis; no residual dysplasia | − | − | − | − | − |
| D. R. | 37 | diploid | pap smear suggestive of dysplasia | − | − | − | − | − |
| S. S. | 52 | — | cone for abnormal pap smear; only degenerative changes | − | − | − | − | − |
| N. A. | 54 | — | ˆCINII removed by laser surgery | − | − | − | − | − |
| J. F. | 50 | diploid | solid ovarian mass; 1 episode of post-menopausal bleeding | + | − | − | − | − |
| V. S. | 60 | diploid | post-menopausal bleeding; no carcinoma diagnosed | − | − | − | − | − |
| D. A. | 39 | — | cervical carcinoma In situ; no evidence of dysplasia or malignancy | − | − | − | − | − |
| E. P. | 45 | diploid | initial curettage suggested endometrial carcinoma, but negative after reexamination | − | − | − | − | − |
| C. N. | 32 | — | ˆCINIII removed by laser surgery | − | − | − | − | − |
| N. T. | 52 | — | ˆCINII removed by laser surgery | − | − | − | − | − |
| F. S. | 35 | diploid | ˆCINIII; following biopsy, no ˆCIN observed | − | − | − | − | − |
| J. I. | 22 | — | right ovarian cyst | − | − | + | − | − |
| A. H. | 24 | — | for dilatation and curettage; on mini-pill | + | − | − | − | − |
| D. E. | 59 | — | ˆCINIII; following biopsy, no ˆCIN observed | − | − | − | − | − |
| J. F. | 24 | — | for dilatation and curettage | − | − | − | − | − |
| K. F. | 26 | diploid | for dilatation and curettage | − | − | − | − | − |
| A. V. | 36 | diploid | ˆCINIII on smear; from biopsy, no dysplasia observed | − | − | − | − | − |
| M. D. | 43 | diploid | ˆCINI; cone and dilatation and curettage | − | − | − | − | − |
| D. W. | 25 | — | for dilatation and curettage, hysteroscopy | − | − | − | − | − |
| M. B. | 48 | — | NIDDM; menorrhagia; for dilation and curettage, hysteroscopy | + | − | − | − | − |
| S. D. | | — | irregular periods; diagnosed with Type II diabetes (NIDDM) | − | − | − | − | − |
| J. F. | 34 | — | ˆCINIII on smear; for cone biopsy | − | − | − | − | − |
| J. O. | 26 | — | cervical carcinoma In situ; for cone biopsy | − | − | − | − | − |
| L. M. | 32 | — | ˆCINI; low dysplasia; on contraception withdrawal | − | − | − | − | − |
| J. K. | 23 | — | for dilatation and curettage, hysteroscopy, pelvoscopy | − | − | − | − | − |
| A. O. | 48 | — | ˆCINIII and irregular periods; for cone biopsy | − | − | − | − | − |
| C. A. | 47 | — | cervical adenocarcinoma In situ; for cone biopsy* | − | − | − | − | − |
| A. K. | 70 | — | on Tamoxifen; past-menopausal bleeding; thickened endometrium; complex pelvic mass; for total abdominal hysterectomy (TAH) . . . benign, atrophic sessile polyps. | − | − | − | − | − |
| C. Di. | 71 | — | post-menopausal bleeding, smears normal; TAH for endometrial polyps | − | − | − | − | − |
| G. L. | 62 | — | post-menopausal bleeding: curetting suggests fragments of regeneration, no atypia. | + | − | − | − | − |
| G. M. | 67 | — | endometrium shows features consistent with Tamoxifen exposure | − | − | − | − | − |

TABLE 2-continued

Summary of current results comparing various parameters in the control group.

| | | DNA | | MMP Expression* | | | | |
|---|---|---|---|---|---|---|---|---|
| Patient Name | Age | Ploidy Status | Clinical Notes | latent MMP-2 | active MMP-2 | putative dimeric MMP-9 | pro-MMP-9 | active MMP-9 |
| N. L. | 54 | — | curetting show no abnormal tissue; cone biopsy shows single focus of high grade abnormality | + | – | – | – | – |
| P. A. | 48 | — | carcinoma in situ on cane biopsy | – | – | – | – | – |
| D. R. | 61 | — | endometrial polyps, on Tamoxifen | – | – | – | – | – |
| S. N. | 31 | — | curetting shows no evidence of hyperplasia or malignancy | – | – | – | – | – |
| L. R. | 61 | — | on Tamoxifen; benign endometrial polyp | – | – | – | – | – |
| L. G. | 46 | — | for dilatation and curettage, hysteroscopy | – | – | – | – | – |
| N. K. | 47 | — | Initially: complex hyperplasia After curette: proliferative endometrium; no hyperplasia or dysplasia | – | – | – | – | – |
| B. M. | | — | For cone biopsy | – | – | – | – | – |
| A. I | 73 | diploid | post-menopausal bleeding, hysteroscopy suggested complex hyperplasia; pathological diagnosis after TAH found a benign endometrial polyp | – | – | – | – | – |

*All uterine irrigation samples were diluted 1:40;
Zymography results based on a scoring system related to size and density of enzyme bands: none (–), very low (+), low (++), moderate (+++), high (++++), very high (+++++).
carcinoma In situ (CIN)

EXAMPLE 2

ELISA Assay of MMP-9 and MMP-2

The Biotrak™ MMP-9 ELISA kit (Calbiochem®), provides a simple and specific determination of MMP-9 in uterine washing samples. The sensitivity of the assay is 0.6 ng/ml. The assay uses two antibodies directed against different epitopes of MMP-9. Any MMP-9 present in the samples or the standards is bound to a microtitre plate precoated with anti-MMP-9. This is followed by a second incubation step, in which a detection antibody conjugated to horseradish peroxidase is added and an immobilised complex is formed. The amount of peroxidase complex in each well is determined by a colour reaction that involves the addition of tetramethylbenzidine substrate to each well. The resultant blue colour is measured at 630 nm in a microtitre plate spectrophotometer (Beckman).

A standard curve is generated by plotting the mean optical density at 630am against ng/ml of standard. From this, the concentration (ng/ml) of each sample is determined by extrapolation from the graph.

One microtitre plate (96 wells) allows for the construction of one standard curve and the measurement of 40 unknowns in duplicate. The ELISA protocol enables results to be obtained in one day.

Figure 1:
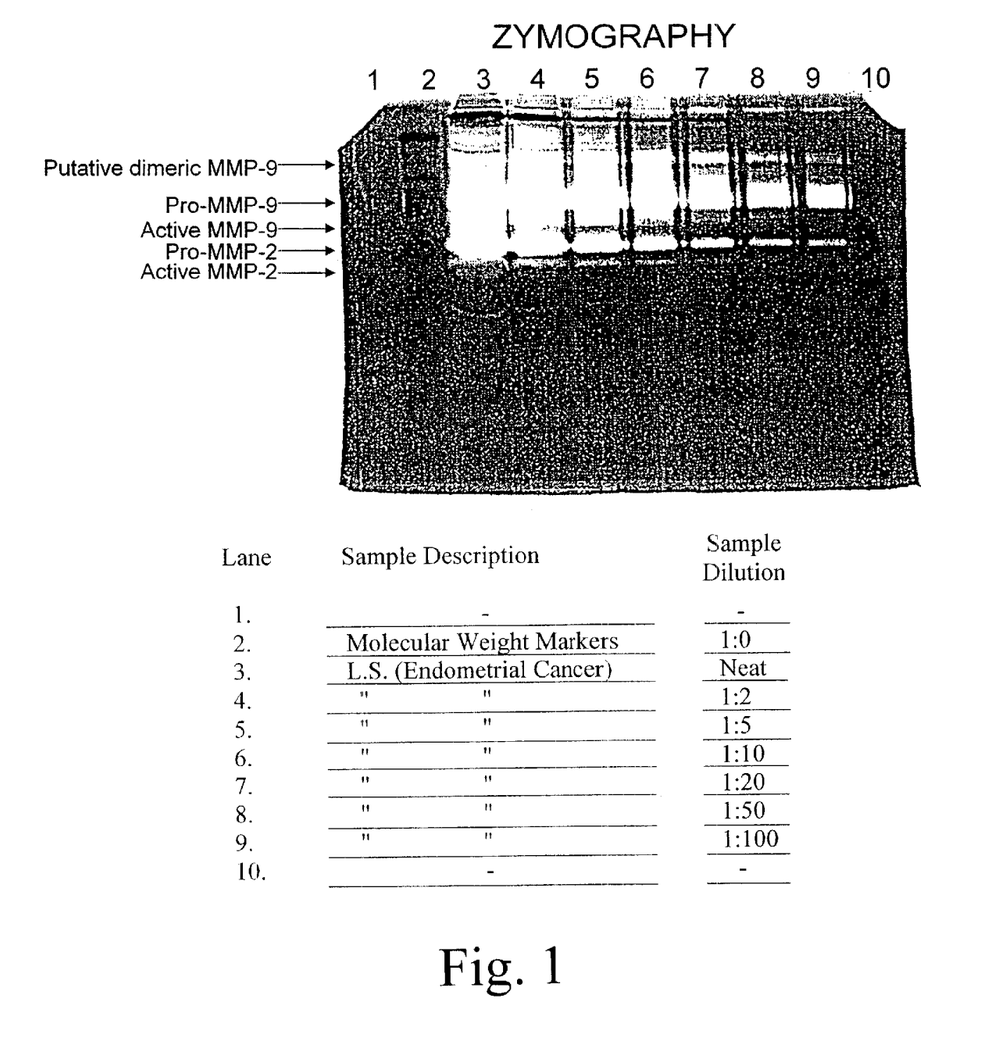
FIG. 1 shows the results of zymography using serial dilutions of a sample of uterine washings from a patient with endometrial cancer.
Figure 2:
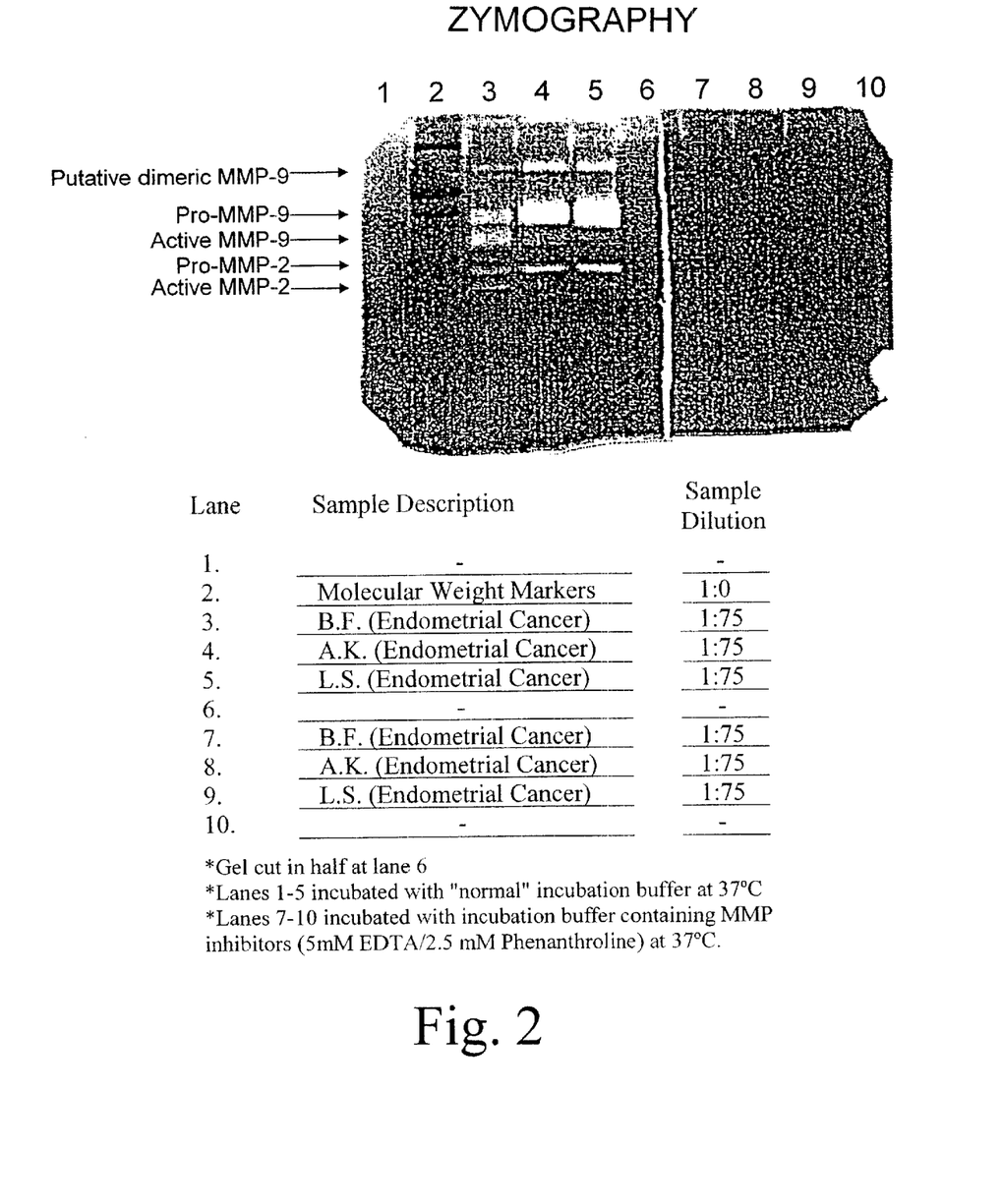
FIG. 2 compares results obtained with a series of samples of uterine washings from patients with endometrial cancer, in which zymography was performed in the absence (left-half of gel) or presence (right-half of gel) of specific inhibitors of MMP activity.
Figure 3A:
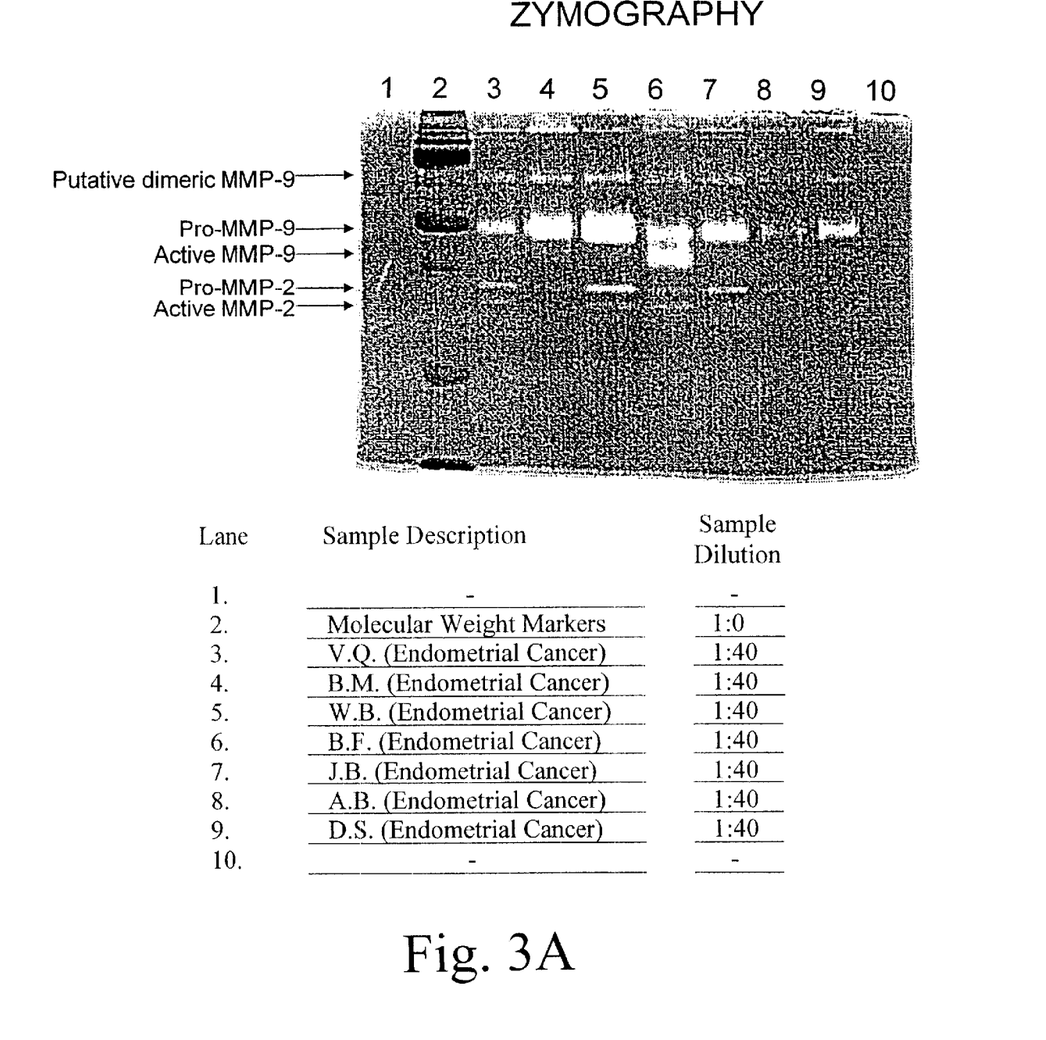
Figure 3B:
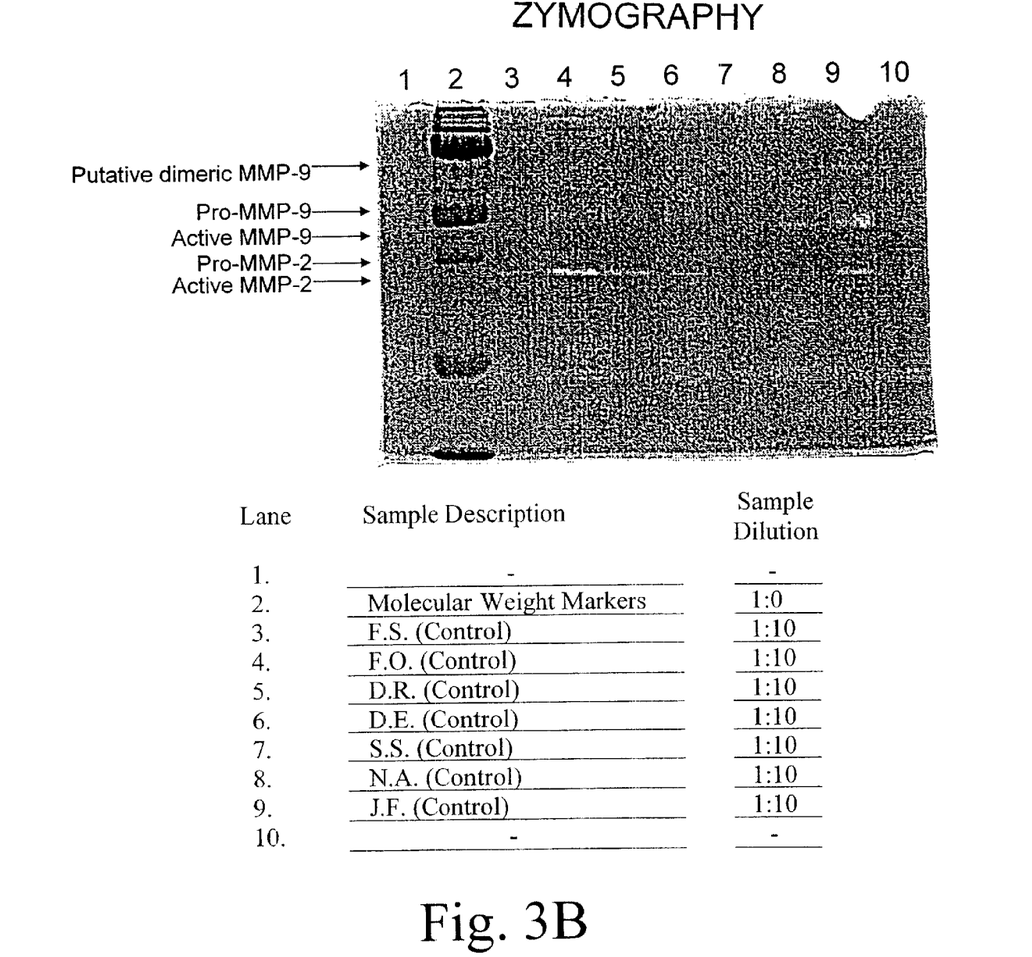
Figure 4:
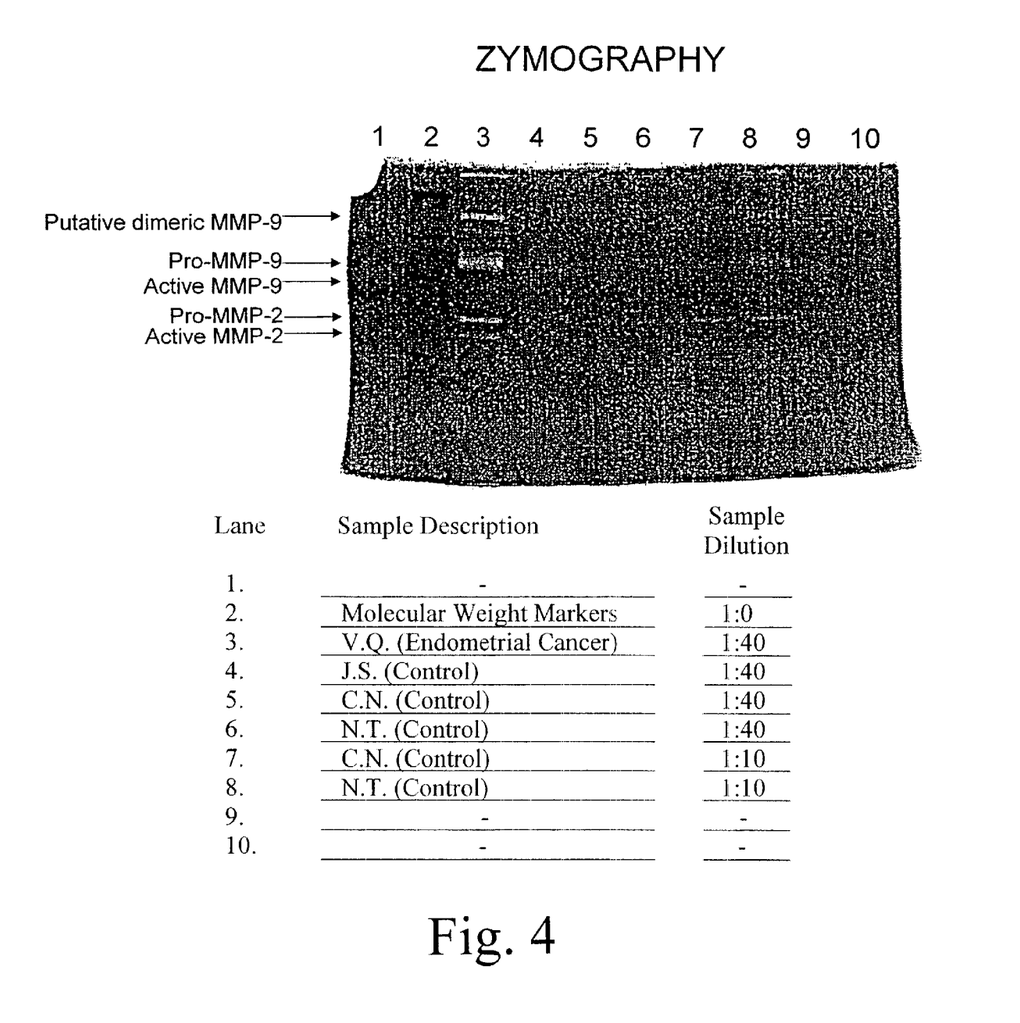
FIG. 4 compares zymography results for a sample of uterine washings from a patient with endometrial cancer (Lane 3) with samples from various control subjects. Lanes 5 and 7 and 6 and 8 respectively are from the same subjects; however the samples in Lanes 7 and 8 are at four times the concentration of those in Lanes 5 and 6.
Figure 5:
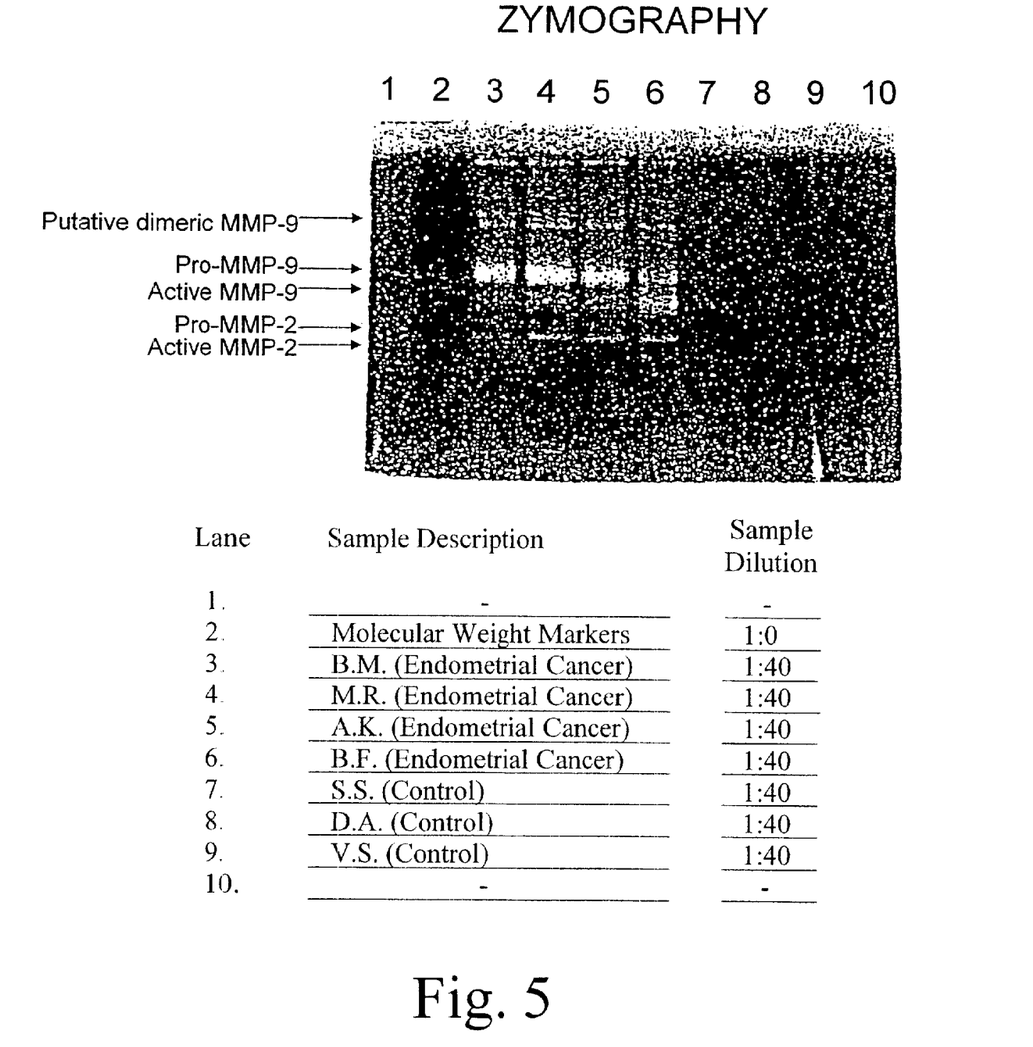
FIGS. 5 and 6 each show a series of different samples from patients with endometrial cancer, run at the same concentration in order to enable direct comparison between samples.
Figure 6:
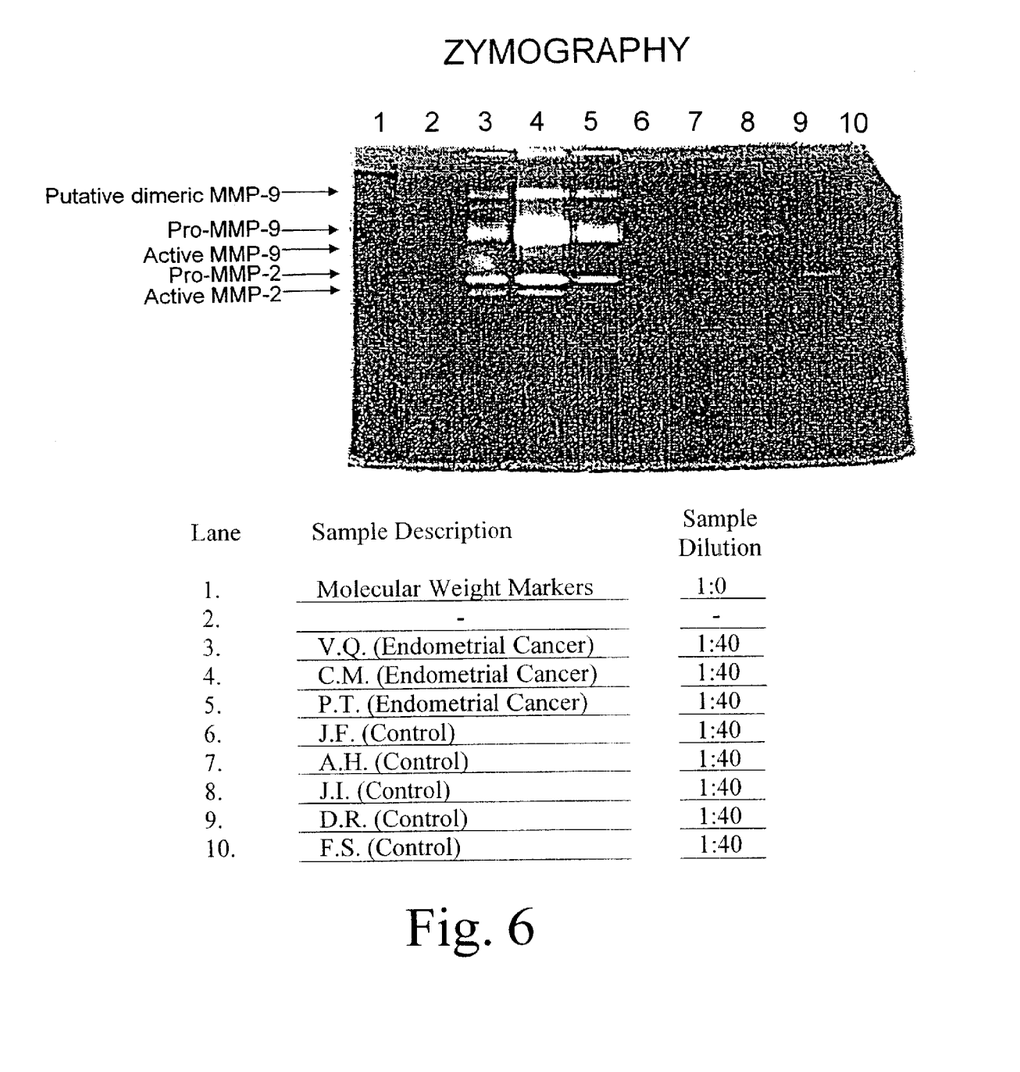
Figure 7:
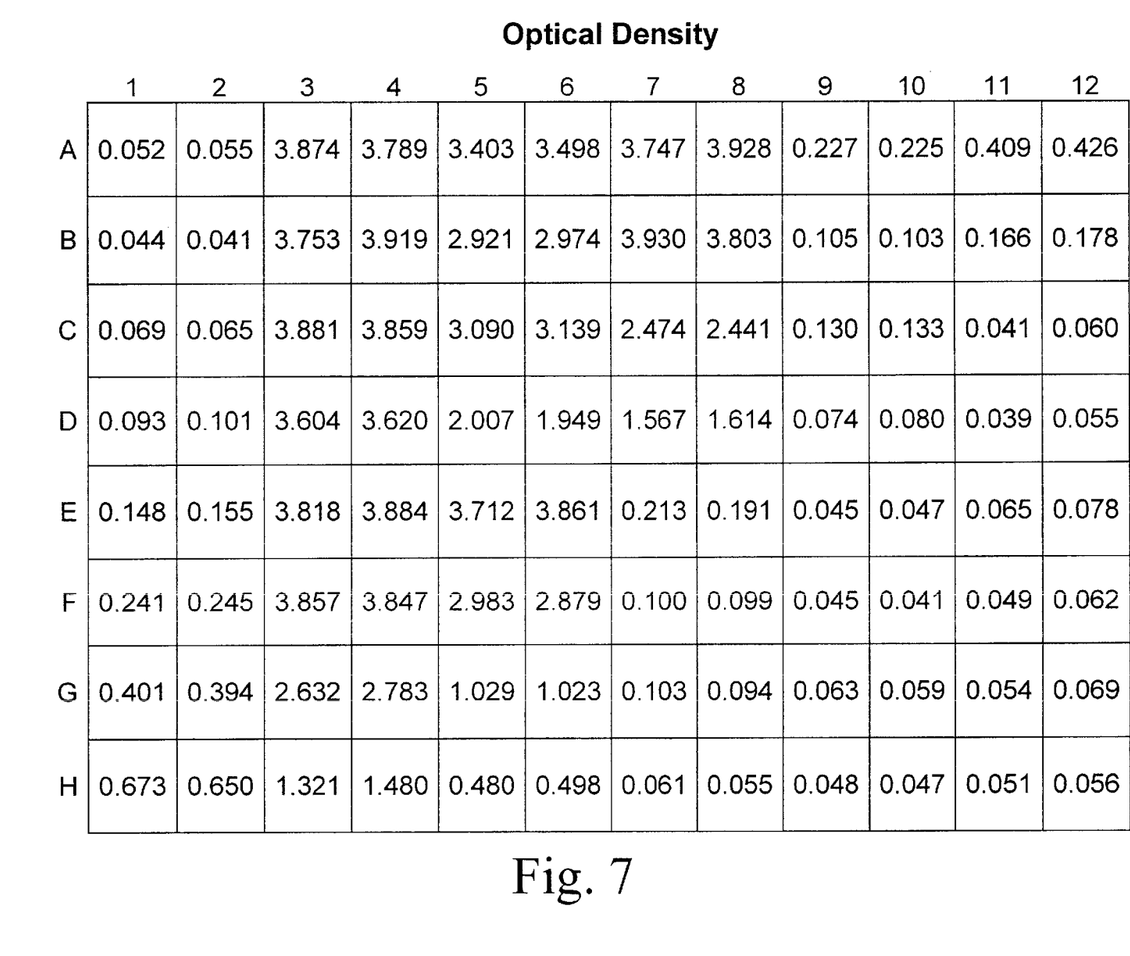
FIG. 7 shows the results of ELISA assay of MMP-9, showing optical density for each well in the microtitre plate.
Figure 8:
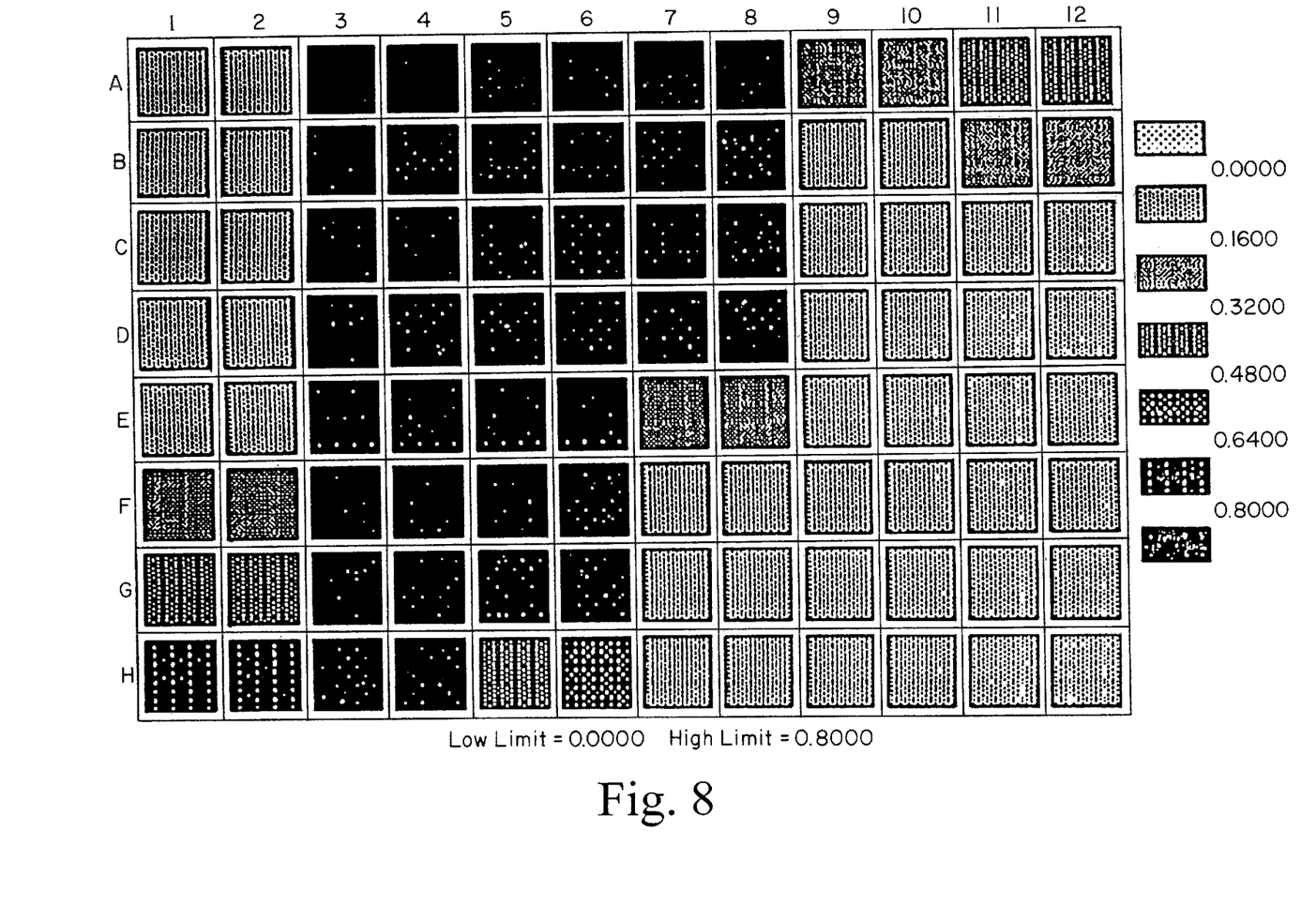
FIG. 8 shows a grey-scale representation of the colour reaction in the microtitre plate.

Samples from 10 cancer and 10 control patients were prepared undiluted and diluted 1:4 and then assayed for presence or absence of MMP-9. FIG. 7 represents the raw data, where the optical density for each well in the microtitre plate is shown. FIG. 8 is a grey-scale representation of the resultant colour reaction in the microtitre plate; this in turn, is a crude representation of the amount of MMP-9 present in the uterine wash samples. All cancer samples have an optical density value significantly above the controls, so much so that the measured values of the cancer samples were outside of the standard curve. As a continuation of this work, a number of samples are serially diluted and assayed using the ELISA test. This titration procedure establishes cut-off values or basal levels of MMP-9 (in ng/ml) for detecting uterine cancer.

This method may also be used to measure MMP-2, using a Biotrak™ MMP-2 ELISA kit, also purchased from Calbiochem®.

EXAMPLE 3

Cell Biology Studies

In patients known to have uterine cancer, a hysterectomy was performed as part of the treatment procedure. After resection of the uterus, where possible, endometrial tissues were excised from two sites:

(a) at the site corresponding to the location of the malignant lesion, and (b) at a site where the endometrium appeared to be normal on macroscopic examination.

Both tumour and normal tissue samples were homogenised in 5 mM Tris-HCl buffer (pH 7.5), containing 0.15M NaCl, 10 mM $CaCl_2$, and 0.05% Brij 35, on ice. Supernatants were obtained by centrifugation, and the protein concentrations were determined by the dye binding method using the BioRad protein assay reagent.

MMP expression in the tissue homogenates was examined by gelatin zymography. The supernatants, corrected for the same amount of protein per lane, were subjected to SDS-PAGE using gelatin impregnated gels as described above.

The zymograms indicated that both MMP-9 and MMP-2 were released from all tissue samples. It was clear, however, that tissue samples from the region of normal endometrium released significantly lower levels of MMP than did tumour tissue samples from the same patient. Thus there appeared to be an upregulation, particularly of MMP-9, in the tumour tissue.

These studies indicate that the elevated levels of MMP-9 and MMP-2, detected by means of the invention that was described in the previous sections, were derived predominantly from secretions of the cancer tissue present in the uterus, rather than being derived from non-human tissue.

EXAMPLE 4

Culture of Endometrial Cancer Cells

Endometrial tissue derived from the site of the tumour was excised from the uterus following hysterectomy as described above. This tissue sample was dissected into smaller pieces, and then washed in alpha-Minimum Essential Medium (MEM) containing 10% FCS. The tumour tissue fragments were then incubated at 37° C. for 40 minutes in a collagenase/MEM solution without FCS. The dissociated cells were washed in MEM +10% FCS and then seeded onto 7 cm$^2$ culture dishes.

The vigorously growing cells became confluent in 3 to 4 days, and appeared to comprise a morphologically homogeneous population of cells. In contrast, epithelial cells derived from a normal region of endometrium failed to establish adequate monolayers in the same period of time. When the tumour cells became confluent the culture medium was replaced with serum-free MEM. The cells were cultured under serum-free conditions for 24 hours before the medium was collected to determine the profile of secreted MMPs by zymography.

Both pro-MMP-2 and pro-MMP-9 were identified on the gels. This study indicated that the cultured cancer cells secrete a similar enzyme profile to that secreted by the cancer cells in the uterine cavity.

EXAMPLE 5

Immunoblotting

Samples of uterine washings were subjected to SDS-PAGE using 10% gels. The samples were run under reducing conditions, and they were then transferred onto a polyvinylidene difluoride membrane. The membrane was washed in blocking buffer before being probed with a monoclonal MMP-2 antibody (IM33L, Calbiochem®). This was followed by three 10 minute washes in TBS (pH 7.4) and incubation of the membrane with a detection antibody conjugated to horseradish peroxidase. A chemiluminescence reaction was then used to detect the immobilised MMP-2 antigen. In this reaction the horseradish peroxidase enzyme catalyses light emission from the oxidation of the luminol reagent. An enhancer reagent was used to increase the emission. The light emitted, which is dependent on the amount of antigen on the membrane, was captured on autoradiography film, producing a permanent record of the results. MMP-9 was detected in the same way using a specific monoclonal MMP-9 antibody (IM37L, Calbiochem®).

This technique clearly defined the identity of the enzymes detected in the uterine washings of patients with endometrial cancer. The imzmmoblotting showed that the two major enzymes detected by zymography were MMP-2 and MMP-9. Additional bands were also detected, but the molecular nature of these gelatinases is yet to be identified. Provisionally, these are regarded as being alternative forms of MM-2 and MMP-9 (for example the putative forms of MMP-2 and MMP-9 shown in Table 1).

EXAMPLE 6

Uterine Ultrasound and Uterine Fluid MMP Analysis for Detection of Endometrial Cancer The aim of this prospective trial was to evaluate the sensitivity and specificity of uterine fluid MMP assays for detecting endometrial cancer in women being investigated for abnormal uterine bleeding by vaginal ultrasonography. Since the investigation involved saline infusion hysterosonography, an initial uterine wash sample was provided for analysis of MMPs in our laboratory in patients who consented to have the test. The population being investigated comprises peri- and post-menopausal women aged 45 to 65 years. This study was expected to reveal the incidence of elevated levels of uterine MMPs in a population of women with a higher risk of having uterine cancer than age matched asymptomatic women. The incidence of endometrial cancer in the population at risk has been estimated to range from 2 to 10%.

Table 3 summarises the results obtained. Of the 105 patients in whom uterine fluid was studied by gelatine zymography, 8 (7.6%) patients had elevated levels of MMPs. Of the 8 patients with a positive MMP test, 5 were found to have uterine cancer by histopathological examination of their endometrial tissues. In the other 3 patients no abnormalities were detected by histological examination. Nonetheless, the elevated levels of MMPs in the uterine fluid may warrant a regular follow-up of such patients, particularly to determine whether this elevation is associated with an increased risk of developing uterine cancer. No false negative results were obtained.

TABLE 3

Analysis of MMPs in the uterine fluid of patients being investigated for abnormal uterine bleeding by means of saline infusion hysterosonography.

| Outcome of NMP | Patients with Histologically Proven Cancer in the Uterus | | |
|---|---|---|---|
| Zymography | YES | NO | Total |
| MMPs Elevated | 5 | 3 | 8 |
| MMPs Basal | 0 | 97 | 97 |
| Total | 5 | 100 | 105 |

Based on the population studied to date it may be concluded that:
1. The sensitivity of the test was 100% (5 elevated MMPs out of 5 cancers detected).
2. The specificity of the test was 97% (97 basal MMPs out of 100 patients who did not have cancer).
3. The predictive value of the test was 62.5% (5 cancers out of a total of 8 patients with elevated MMPs).

We have found that the uterine secretions of all women with endometrial cancer in the present study contained markedly elevated levels of MMP-2 and MMP-9, compared with absent or very low levels in the uterine secretions of the control group. This distinct and consistent difference in enzyme levels between the cancer and control groups strongly suggests that MMP analysis in uterine secretions is useful as a sensitive and reliable diagnostic test for all grades of endometrial carcinoma.

Since uterine irrigation is a relatively simple and non-intrusive procedure, assay of the uterine washing samples by gelatin zymography, or an alternative means of MMP assay, such as ELISA can be used as a routine screening test for endometrial malignancy, optionally in conjunction with a Pap smear for cervical disease. Preliminary statistical analysis suggests that the sensitivity of the test according to the invention is 100%. This compares very favourably to the sensitivity of 80% usually observed with the conventional Pap smear. ELISA or chemiluminescent assays can readily be automated, and are suitable for use in large-scale screening and in clinical trials.

In addition, our current findings strongly suggest that MMP-2 and MMP-9 are involved in endometrial cancer growth, and probably in the spread of the tumour in the uterus. This may provide the rationale for using specific enzyme inhibitors, together with other treatment modalities, in the overall management of uterine cancers.

The number of patients for each grade of endometrial adenocarcinoma was too small to draw any conclusions about the level of MMP-2 and MMP-9 in relation to histological grade or depth of myometrial invasion. In general, however, the highest levels of both MMPs were found in the two patients that had the deepest invasion. Each of these women was also found to have polyploid tumour cells and an estimated moderate malignancy grade (Table 1). This suggests that the levels of MMP-2 and MMP-9 provide a useful supplement to previously-known prognostic indicators.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Baak, J. P. A. Manual of Quantitative Pathology in Cancer Diagnosis and Prognosis, 1991
Barrett, A. J. Methods in Enzymology, Proteolytic Enzymes, Aspartic and Metallo Peptidases, 1995 248 413–528
Berchuck, A. et al Gynecol. Oncol., 1992 44 61–65
Bocking A. et al Anal. Quant. Cytol., 1984 61–8
Iversen, O. E. Am. J. Obstet. Gynecol., 1986 155 770–776
Jeziorska, M., Salamonsen, L. A. and Woolley, D. E. J. Reprod. Fertil., 1996 107 43–51
Keiner D. E. and Stetler-Stevenson, W. G. Anal. Biochem., 1994 218 3235–3329
Liotta, L. A. et al Ann. Rev. Biochem., 1986 55 1037–1057
Lukes, A. S. et al Cancer, 1994 73 2380–2385
Moberger, B. et al Cytometry., 1985 5 430–436
Podratz, R. C. et al Am. J. Obstet. Gynecol., 1993 168 1206–1215
Rawdanowicz, T. J., Hampton, A. L., Nagase, H., Woolley, D. E. and Salamonsen, L. A. J. Clin. Endocrinol. Metab., 1994 79 530–536
Sakuragi, N. et al Gynecol. Oncol., 1994 53 183–189
Salamonsen, L. A. Trends in Endocrinology, 1996 7 28–34
Salamonsen, L. A., Nagase, H. and Woolley, D. E. J. Cell. Sci., 1991 100 381–385
Salamonsen, L. A., Nagase, H. and Woolley, D. E. J. Reprod. Fertil. Suppl., 1995 49 29–37
Salamonsen, L. A., Nagase, H., Suzuki, R. and Woolley, D. E. J. Reprod. Fertil., 1993 98 583–589
Salamonsen, L. A. and Woolley, D. E. Human Reprod., 1996 11 Suppl. 2 124–133
Seckinger, D. et al Arch. Pathol. Lab. Med., 1989 113 619–626
Stetler-Stevenson, W. G. et al Ann. Rev. Cell Biol., 1993 9 541–573
van der Putten, H. W. H. M. et al Cancer, 1989 63 1378–1387

What is claimed is:

1. A method of detecting the presence of endometrial cancer in a subject at risk of, or suspected to be suffering from, endometrial cancer, comprising the steps of obtaining a sample of uterine fluid from the uterine cavity of the subject, and measuring the levels or activity of matrix metalloproteinase-2 (MMP-2) and/or matrix metalloproteinase-9 (MMP-9) in the uterine fluid, wherein an elevated level or activity of MMP-2 and/or MMP-9 in the fluid from the subject as compared to a control indicates that endometrial cancer is present in the subject, thereby detecting the presence of endometrial cancer.

2. A method according to claim 1, in which total gelatinolytic enzymes in the uterine fluid are measured.

3. A method according to claim 1, in which MMP activity is detected by zymography.

4. A method according to claim 3, in which levels of MMP-2 and MMP-9 are measured by quantitative densitometric zymography.

5. A method according to claim 3, in which densitometric measurement of MMP activity is also performed.

6. A method according to claim 1, in which total enzyme levels are measured using Enzyme-linked Immunosorbent Assay (ELISA), fluorometric assay, chemiluminescent assay, or radioimmunoassay.

7. A method according to claim 6, in which MMP levels are measured by chemiluminescent assay.

8. A method according to claim 6, in which MMP levels are measured by ELISA.

9. A method according to claim 1, in which levels of tissue inhibitors of metalloproteinases in the uterine fluid are also measured.

10. A method according to claim 1, in which
  a) a sample of superficial endometrial cells is collected at the same time as the uterine fluid is obtained,
  b) the endometrial cells are subjected to cytological examination for determination of ploidy and morphometry, and
  c) levels of MMPs in the uterine fluid are correlated with DNA ploidy as an indicator of the prognosis of endometrial cancer when endometrial cancer is present.

11. A method according to claim 1, wherein the sample of uterine fluid comprises diluted uterine fluid.

12. A method according to claim 11, in which the MMP activity of a cell-free sample of uterine washings is measured.

13. A method according to claim 1, wherein the subject at risk of endometrial cancer is peri-menopausal or post-menopausal, genetically predisposed to endometrial cancer, or is taking medication which has endometrial cancer as a potential side-effect.

14. A method of detection of recurrence of endometrial cancer in a patient who has undergone conservative treatment for primary endometrial cancer, comprising the steps of obtaining a sample of uterine fluid from the uterine cavity of the patient, and measuring the levels or activity of MMP-2 and/or MMP-9 in the fluid, wherein an elevated level or activity of MMP-2 and/or MMP-9 in the fluid from the patient as compared to a control indicates that endometrial cancer has recurred in the patient, thereby detecting the recurrence of endometrial cancer.

15. A method according to claim 14, wherein the sample of uterine fluid comprises diluted uterine fluid.

16. A method according to claim 15, in which MMP activity of a cell-free sample of uterine washings is measured.

17. A method of detecting the presence or recurrence of endometrial cancer in a subject, comprising:
  obtaining a sample of uterine fluid from the uterine cavity of the subject, and
  measuring the level or activity of MMP-2 and/or MMP-9 in the fluid,
wherein an elevated level or activity of MMP-2 and/or MMP-9 in the fluid from the subject as compared to a control indicates that endometrial cancer is present or has recurred in the patient, thereby detecting the presence or recurrence of endometrial cancer.

18. A method according to claim 17, wherein the sample of uterine fluid comprises diluted uterine fluid.

19. A method according to claim 18, in which MMP activity of a cell-free sample of uterine washings is measured.

20. A method according to claim 14 or 17, in which total gelatinolytic activity in the uterine fluid is measured.

21. A method according to claim 14 or 17, in which MMP activity is detected by zymography.

22. A method according to claim 21, in which densitometric measurement of MMP activity is also performed.

23. A method according to claim 14 or 17, in which enzyme levels are measured using ELISA, fluorometric assay, chemiluminescent assay, or radioimmunoassay.

24. A method according to claim 23, in which MMP levels are measured by chemiluminescent assay.

25. A method according to claim 23, in which MMP levels are measured by ELISA.

26. A method of monitoring the efficacy of a putative treatment for endometrial cancer in a patient, comprising the steps of obtaining a sample of uterine fluid from the uterine cavity of the patient before and after the patient has received the putative treatment, measuring the levels or activity of MMP-2 and/or MMP-9 in fluid, wherein lowered levels or activities of MMP-2 and/or MMP-9 in the sample taken after treatment relative to the sample taken before treatment indicates that the putative treatment is succeeding, thereby monitoring the efficacy of the putative treatment for endometrial cancer.

27. A method according to claim 26, in which total gelatinolytic activity in the uterine fluid is measured.

28. A method according to claim 26, in which MMP activity is detected by zymography, optionally in conjunction with densitometric measurement.

29. A method according to claim 28, in which densitometric measurement of MMP activity is also performed.

30. A method according to claim 26, in which enzyme levels are measured using ELISA, fluorometric assay, chemiluminescent assay, or radioimmunoassay.

31. A method according to claim 30, in which MMP levels are measured by chemiluminescent assay.

32. A method according to claim 30, in which MMP levels are measured by ELISA.

33. A method according to claim 30, in which levels of MMP-2 and/or MMP-9 are measured by quantitative densitometric zymography or ELISA.

34. A method according to claim 26, wherein the sample of uterine fluid comprises diluted uterine fluid.

35. A method according to claim 34, in which MMP activity of a cell-free sample of uterine washings is measured.

36. A kit detecting for the presence or recurrence of endometrial cancer in a subject, comprising:
    (a) a suitable diluent for irrigating the uterine cavity of the subject, and
    (b) a means for delivery, recovery and collection of the diluted uterine fluid, and
    (c) a means for determining the level or activity of MMP-2 and/or MMP-9 in said diluted fluid.

37. A kit according to claim 36, further comprising one or more of:
    (a) a means for taking a sample of endometrial epithelium,
    (b) one or more microscope slides, and
    (c) a receptacle containing a histological fixative.

38. A kit according to claim 36, comprising:
    (a) a sterile physiologically-acceptable solution for irrigating the uterine cavity of the subject,
    (b) a sterile syringe,
    (c) a sterile tube or catheter,
    (d) a receptacle for receiving the diluted uterine fluid, and optionally,
    (e) a means for determining the level of MMPs in said diluted fluid,
    (f) a uterine brush, and/or
    (g) at least one microscope slide.

39. A kit according to claim 38, additionally comprising a receptacle containing a histological fixative.

40. A kit according to claim 38, in which the fixative is 4% paraformaldehyde.

\* \* \* \* \*